(12) United States Patent
Hirawat et al.

(10) Patent No.: US 10,085,996 B2
(45) Date of Patent: Oct. 2, 2018

(54) PHARMACEUTICAL COMBINATIONS

(71) Applicant: NOVARTIS AG, Basel (CH)

(72) Inventors: Samit Hirawat, Chatham, NJ (US); Cristian Massacesi, Neuilly sur-Seine (FR)

(*) Notice: Subject to any disclaimer, the term of this patent is extended or adjusted under 35 U.S.C. 154(b) by 0 days.

(21) Appl. No.: 15/646,494

(22) Filed: Jul. 11, 2017

(65) Prior Publication Data

US 2017/0304311 A1 Oct. 26, 2017

Related U.S. Application Data

(63) Continuation of application No. 15/109,704, filed as application No. PCT/IB2015/050260 on Jan. 13, 2015, now abandoned.

(30) Foreign Application Priority Data

Jan. 15, 2014 (EP) ..................................... 14305057

(51) Int. Cl.
*A61K 31/5377* (2006.01)
*A61K 31/138* (2006.01)
*A61K 31/4439* (2006.01)
*A61K 38/09* (2006.01)
*A61K 45/06* (2006.01)
*A61K 31/4535* (2006.01)

(52) U.S. Cl.
CPC ........ *A61K 31/5377* (2013.01); *A61K 31/138* (2013.01); *A61K 31/4439* (2013.01); *A61K 31/4535* (2013.01); *A61K 38/09* (2013.01); *A61K 45/06* (2013.01)

(58) Field of Classification Search
CPC .............. A61K 31/5377; A61K 31/138; A61K 31/4439
See application file for complete search history.

(56) References Cited

U.S. PATENT DOCUMENTS

| 2012/0035150 A1* | 2/2012 | Gaweco | A61K 31/47 514/210.18 |
|---|---|---|---|
| 2015/0148345 A1 | 5/2015 | Lannutti et al. | |

FOREIGN PATENT DOCUMENTS

| WO | 2011/130342 A1 | 10/2011 |
| WO | 2013/142245 A1 | 9/2013 |

OTHER PUBLICATIONS

Stebbing et al., (Clinical evidence; 2009).*
Masuda et al. (Breast Cancer Res Treat. Apr. 2011;126(2):443-51).*
Elkabets et al. (www.ScienceTranslationalMedicine.org Jul. 31, 2013 vol. 5 Issue 196).*
Cristian Massacesi et al: "Challenges in the clinical development of PI3K inhibitors", Annals of the New York Academy of Sciences, vol. 1280, No. 1, 2013, pp. 19-23, XP055089169.
Todd W Miller et al: "ER[alpha]—dependent E2F transcription can mediate resistance to estrogen deprivation in human breast cancer", Cancer Discovery, vol. 1, No. 4, 2011, pp. 338-351, XP002683182.
Gayathri Nagaraj et al: "A phase 1 study of BKM120, a novel oral selective phosphatidylinositol-3-kinase (PI3K) inhibitor, in combination with fulvestrant in postmenopausal women with estrogen receptor positive metastatic breast cancer.", J Clin Oncol 30, 2012 (suppl; abstr TPS664), 2012, XP055163484.
S.-M. Maira et al: "Identification and Characterization of NVP-BKM120, an Orally Available Pan-Class 1 PI3-Kinase Inhibitor", Molecular Cancer Therapeutics, vol. 11, No. 2, 2012, p. 317-328, XP055043550.
D Juric et al: "Phase 1 study of BYL719, an alpha-specific PI3K inhibitor, in patients with PIK3CA mutant advanced solid tumors: preliminary efficacy and safety in patients with PIK3CA mutant ER-positive (ER+) metastatic breast cancer (MBC)", Cancer Research: Dec. 15, 2012; vol. 72, Issue 24, Supplement 3, Abstract nr P6-10-07, 2012, XP055122102.
Justin Siebbring et al: "Breat cancer (metastatic)" Women's Health, Clinical Evidence, 2010, 9:811, p. 1-41.
Norikazu Masuda et al: "Monthly versus 3-monthly goserelin acetate treatment in pre-menopausal patients with estrogen receptor—positive early breast cancer", Breast Cancer Res. Treat. (2011) 126:443-451.

* cited by examiner

*Primary Examiner* — Shirley V Gembeh
(74) *Attorney, Agent, or Firm* — Sandra Rueck

(57) ABSTRACT

A pharmaceutical combination comprising: (a) a phosphatidylinositol-3-kinase inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof and (b) a gonadorelin agonist and, optionally, (c) an antiestrogen agent, particularly for use in the treatment or prevention of a cancer; uses of such a combination in the preparation of a medicament for the treatment or prevention of a cancer; pharmaceutical compositions of the combination of said therapeutic agents and methods of treating a cancer in a subject comprising administering to said subject a therapeutically effective amount of such a combination.

7 Claims, No Drawings

PHARMACEUTICAL COMBINATIONS

FIELD OF THE INVENTION

A pharmaceutical combination comprising: (a) a phosphatidylinositol-3-kinase inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof and (b) a gonadorelin agonist and, optionally, (c) an antiestrogen agent, particularly for use in the treatment or prevention of a cancer; uses of such a combination in the preparation of a medicament for the treatment or prevention of a cancer; pharmaceutical compositions of the combination of said therapeutic agents and methods of treating a cancer in a subject comprising administering to said subject a therapeutically effective amount of such a combination.

BACKGROUND OF THE INVENTION

Phosphatidylinositol 3-kinases (PI-3 kinase or PI3K) comprise a family of lipid and serine/threonine kinases that catalyze the transfer of phosphate to the D-3' position of inositol lipids to produce phosphoinositol-3-phosphate (PIP), phosphoinositol-3,4-diphosphate (PIP2) and phosphoinositol-3,4,5-triphosphate (PIP3) that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., Annu. Rev. Biochem 70:535 (2001); Katso et al., Annu. Rev. Cell Dev. Biol. 17:615 (2001)). Of the two Class 1 PI3Ks, Class 1A PI3Ks are heterodimers composed of a catalytic p110 subunit ($\alpha$, $\beta$, $\delta$ isoforms) constitutively associated with a regulatory subunit that can be p85$\alpha$, p55$\alpha$, p50$\alpha$, p85$\beta$ or p55$\gamma$. The Class 1B sub-class has one family member, a heterodimer composed of a catalytic p110$\gamma$ subunit associated with one of two regulatory subunits, p101 or p84 (Fruman et al., Annu Rev. Biochem. 67:481 (1998); Suire et al., Curr. Biol. 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., Cell 89:105 (1997)); Katso et al., Annu. Rev. Cell Dev. Biol. 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., Cell 64:281 (1991); Escobedo and Williams, Nature 335:85 (1988); Fantl et al., Cell 69:413 (1992)).

PI3K inhibitors are useful therapeutic compounds for the treatment of various conditions in humans. Aberrant regulation of PI3K is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110$\alpha$ isoform, PIK3CA, and for Akt are amplified and increased protein expression of their gene products has been demonstrated in several human cancers. Furthermore, mutations and translocation of p85$\alpha$ that serve to up-regulate the p85-p110 complex have been described in a few human cancers. Finally, somatic missense mutations in PIK3CA that activate downstream signaling pathways have been described at significant frequencies in a wide diversity of human cancers (Kang et al., Proc. Natl. Acad. Sci. USA 102:802 (2005); Samuels et al., Science 304:554 (2004); Samuels et al., Cancer Cell 7:561-573(2005)). These observations show that deregulation of phosphoinositol-3 kinase and the upstream and downstream components of this signaling pathway is one of the most common deregulations associated with human cancers and proliferative diseases (Parsons et al., Nature 436:792(2005); Hennessey at el., Nature Rev. Drug Dis. 4:988-1004 (2005)).

In the last decades, the incidence of breast cancer has been rapidly increasing in many countries. (Minami 2004, Sim 2006, Yoo 2006, Matsuno 2007). Several important hormonal therapies have been developed, but there is no major improvement of hormonal therapy for many types of breast cancer including, for example, pre-menopausal metastatic breast cancer. According to recent NCNN guideline and ESMO guideline, the first line hormonal therapy for pre-menopausal metastatic breast cancer is tamoxifen and/or ovary ablation or suppression therapy. (NCNN guideline 2013, Cardoso 2012). Tamoxifen with ovarian ablation is still the preferred therapy.

Thus, in spite of numerous treatment options for cancer patients, there remains a significant unmet need for effective and safe therapeutic agents for cancer treatment and a need for their preferential use in combination therapy. The compounds 5-(2,6-di-morpholin-4-yl-pyrimidin-4-yl)-4-trifluoromethyl-pyridin-2-ylamine and (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) are novel compounds that selectively inhibit phosphatidylinositol 3-kinase activity. These specific PI3K inhibitors are believed to have a strong beneficial interaction (e.g, synergistic) and/or improved anti-proliferative activity when used in combination with a gonadorelin agonist, particularly when further combined with an antiestrogen agent. It is therefore an object of the present invention to provide for a medicament to improve treatment of cancer.

SUMMARY OF THE INVENTION

The present invention relates to a pharmaceutical combination comprising: (a) a phosphatidylinositol-3-kinase (PI3K) inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof and (b) a gonadorelin agonist and, optionally, (c) an antiestrogen agent, particularly for separate, simultaneous or sequential use for the treatment or prevention of a cancer.

In a preferred embodiment, the present invention relates to a pharmaceutical combination comprising (a) a PI3K inhibitor selected from COMPOUND A, COMPOUND B or any pharmaceutically acceptable salt thereof, and (b) goserelin or any pharmaceutically acceptable thereof, particularly for use in the treatment or prevention of a hormone-receptor positive breast cancer.

In a preferred embodiment, the present invention relates to a pharmaceutical combination comprising (a) a PI3K inhibitor selected from COMPOUND A, COMPOUND B or any pharmaceutically acceptable salt thereof, and (b) goserelin or any pharmaceutically acceptable thereof, and (c) tamoxifen or any pharmaceutically acceptable salt thereof, particularly for use in the treatment or prevention of a hormone-receptor positive breast cancer.

In a further embodiment, the present invention relates to a method of treating or preventing a cancer in a subject comprising administering to said subject a therapeutically effective amount of a COMBINATION OF THE INVENTION.

In a further embodiment, the present invention relates to the use of a COMBINATION OF THE INVENTION for the preparation of a pharmaceutical composition or medicament for the treatment or prevention of a cancer.

In a further embodiment, the present invention relates to the use of a COMBINATION OF THE INVENTION for the treatment or prevention of a cancer.

In a further embodiment, the present invention relates to a pharmaceutical composition or combined preparation, comprising a quantity of COMBINATION OF THE INVENTION which is jointly therapeutically effective against a cancer, and optionally at least one pharmaceutically acceptable carrier.

In a further embodiment, the present invention relates to a combined preparation comprising (a) one or more dosage units of a PI3K inhibitor selected from COMPOUND A, COMPOUND B or any pharmaceutically acceptable salt thereof and (b) one or more dosage units of a gonadorelin agonist and, optionally (c) one or more dosage units of an antiestrogen agent, for use in the treatment or prevention of a cancer.

In a further embodiment, the present invention provides a commercial package comprising as active ingredients of COMBINATION OF THE INVENTION, together with instructions for simultaneous, separate or sequential administration of said combination to a patient in need thereof for use in the treatment or prevention of a cancer.

In a further embodiment, the present invention provides a commercial package comprising as active ingredient a PI3K inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof, and instructions for simultaneous, separate or sequential administration of said active ingredient with a gonadorelin agonist to a patient in need thereof for use in the treatment or prevention of a cancer.

In a further embodiment, the present invention provides a commercial package comprising as active ingredient a PI3K inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof, and instructions for simultaneous, separate or sequential administration of said active ingredient with a gonadorelin agonist and an antiestrogen agent to a patient in need thereof for use in the treatment or prevention of a cancer.

DETAILED DESCRIPTION OF THE INVENTION

The present invention relates to a pharmaceutical combination comprising: (a) a phosphatidylinositol-3-kinase (PI3K) inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof and (b) a gonadorelin agonist and, optionally, (c) an antiestrogen agent, particularly for separate, simultaneous or sequential use for the treatment or prevention of a cancer.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" as used herein defines either a fixed combination in one dosage unit form or a kit of parts for the combined administration where the therapeutic agents may be administered independently at the same time or separately within time intervals that allow that the therapeutic agents show a cooperative, e.g., synergistic, effect.

The term "combined administration" as used herein is defined to encompass the administration of the selected therapeutic agents to a single patient, and are intended to include treatment regimens in which the therapeutic agents are not necessarily administered by the same route of administration or at the same time.

The term "fixed combination" means that the therapeutic agents are administered to a patient simultaneously in the form of a single entity or dosage form.

The term "a combined preparation" is defined herein to refer to especially a "kit of parts" in the sense that the therapeutic agents (a) and (b) as defined above can be dosed independently or by use of different fixed combinations with distinguished amounts of the therapeutic agents (a) and (b) simultaneously or at different time points. The parts of the kit of parts can then, e.g., be administered simultaneously or chronologically staggered, that is at different time points and with equal or different time intervals for any part of the kit of parts. The ratio of the total amounts of the therapeutic agent (a) to the therapeutic agent (b) to be administered in the combined preparation can be varied, e.g., in order to cope with the needs of a patient sub-population to be treated or the needs of the single patient. In embodiments including an antiestrogen agent, the term "combined preparation" refers to especially a "kit of parts" in the sense that therapeutic agents (a), (b) and (c) as defined above can be dosed independently or by use of different fixed combinations with distinguished amounts of the therapeutic agents (a), (b) and (c), i.e., simultaneously or at different time points.

The term "pharmaceutically acceptable" is defined herein to refer to those compounds, materials, biologic agents, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "phosphatidylinositol 3-kinase inhibitor" or "PI3K inhibitor" is defined herein to refer to a compound which targets, decreases or inhibits phosphatidylinositol 3-kinase.

The term "gonadorelin agonist" as used herein, includes, but is not limited to, abarelix, goserelin, buserelin, or any pharmaceutically acceptable salt thereof. Goserelin is disclosed in U.S. Pat. No. 4,100,274 and is marketed as ZOLADEX®. Abarelix can be formulated, e.g., as disclosed in U.S. Pat. No. 5,843,901. Buserelin is marketed as SUPREFACT®.

The term "antiestrogen agent" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX®. Raloxifene hydrochloride can be administered, e.g., in the form as it is marketed, e.g. under the trademark EVISTA®. Fulvestrant can be formulated as disclosed in U.S. Pat. No. 4,659,516 or it can be administered, e.g., in the form as it is marketed, e.g. under the trademark FASLODEX®. A combination of the invention comprising an antiestrogen agent is particularly useful for the treatment of estrogen receptor positive tumors, e.g. breast tumors.

The term "treating" or "treatment" as used herein comprises a treatment relieving, reducing or alleviating at least one symptom in a subject or effecting a delay of progression of a cancer. For example, treatment can be the diminishment of one or several symptoms of a cancer or complete eradication of a cancer. Within the meaning of the present invention, the term "treat" also denotes to arrest, delay the onset (i.e., the period prior to clinical manifestation of a cancer) and/or reduce the risk of developing or worsening a cancer. The term "prevention" is used herein to mean prevent, delay or treat, or all, as appropriate, development or continuance or aggravation of a cancer in a subject.

The term "joint therapeutic effect" or "jointly therapeutically effective" means that the therapeutic agents of the combination may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both or all therapeutic agents are present in the blood of the human to be treated at least during certain time intervals.

The term "effective amount" or "therapeutically effective amount" of a combination of therapeutic agents is an amount sufficient to provide an observable improvement over the baseline clinically observable signs and symptoms of the cancer treated with the combination.

The term "synergistic effect" as used herein refers to action of two therapeutic agents such as, for example, (a) a PI3K inhibitor, and (b) a gonadorelin agonist, producing an effect, for example, slowing the symptomatic progression of a cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. Synergy may be further shown by calculating the synergy score of the combination according to methods known by one of ordinary skill. When the embodiment includes an antiestrogen agent, the term "synergistic effect" as used herein refers to action of three therapeutic agents such as, for example, (a) a PI3K inhibitor, (b) a gonadorelin agonist, and (c) an antiestrogen agent, producing an effect, for example, slowing the symptomatic progression of a cancer or symptoms thereof which is greater than the simple addition of the effects of each drug administered by themselves or greater than either dual therapy.

The term "subject" or "patient" as used herein includes animals, which are capable of suffering from or afflicted with a cancer. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from a cancer.

The term "about" or "approximately" shall have the meaning of within 10%, more preferably within 5%, of a given value or range.

A "pharmaceutically acceptable salt", as used herein, unless otherwise indicated, includes salts of acidic and basic groups which may be present in the compounds of the present invention. Such salts can be prepared in situ during the final isolation and purification of the compounds, or by separately reacting the base or acid functions with a suitable organic or inorganic acid or base, respectively. Suitable salts of the compound include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2 hydroxyethanesulfonate, lactate, maleate, methanesulfonate, nicotinate, 2 naphthalenesulfonate, oxalate, pamoate, pectinate, persulfate, 3 phenylproionate, picrate, pivalate, propionate, succinate, sulfate, tartrate, thiocyanate, p toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others.

The present invention relates to a pharmaceutical combination comprising: (a) a phosphatidylinositol-3-kinase (PI3K) inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof and (b) a gonadorelin agonist and, optionally, (c) an antiestrogen agent, particularly for separate, simultaneous or sequential use for the treatment or prevention of a cancer.

Phosphatidylinositol-3-kinase (PI3K) inhibitors suitable for the present invention are selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof.

WO07/084786 describes specific pyrimidine derivatives which have been found to inhibit the activity of PI3K. The compound 5-(2,6-di-morpholin-4-yl-pyrimidin-4-yl)-4-trifluoromethyl-pyridin-2-ylamine (hereinafter "COMPOUND A") has the chemical structure of formula (I)

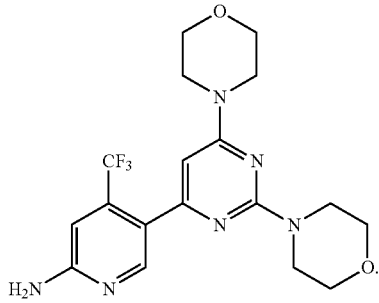

(I)

The compound 5-(2,6-di-morpholin-4-yl-pyrimidin-4-yl)-4-trifluoromethyl-pyridin-2-ylamine, its salts, its utility as a PI3K inhibitor and synthesis of the compound are described in WO 2007/084786, which is hereby incorporated by reference in its entirety hereto, for instance in Example 10. COMPOUND A may be present in the form of the free base or any pharmaceutically acceptable salt thereto. Preferably, COMPOUND A is in the form of its hydrochloride salt.

ylic acid 2-amide 1-({4-methyl-5-[2-(2,2,2-trifluoro-1,1-dimethyl-ethyl)-pyridin-4-yl]-thiazol-2-yl}-amide) (hereinafter "COMPOUND B") has the chemical structure of formula (II)

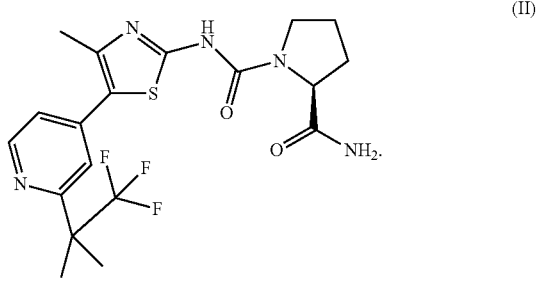 [SMILES: Cc1nc(NC(=O)N2CCC[C@H]2C(N)=O)sc1-c1ccnc(C(C)(C)C(F)(F)F)c1]

(II)

The compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), its salts, its utility as an alpha-isoform selective PI3K inhibitor and synthesis of the compound are described in WO2010/029082, which is hereby incorporated by reference in its entirety, for instance in Example 15. COMPOUND B may be present in the form of the free base or any pharmaceutically acceptable salt thereto. Preferably, COMPOUND B is in the form of its free base.

Gonadorelin agonists are known in the art. Gonadorelin agonists particularly suitable for use in the present invention include, but is not limited to, abarelix, goserelin, buserelin, or any pharmaceutically acceptable salts thereof.

Abarelix is disclosed in U.S. Pat. No. 5,843,901 and has the following chemical structure:

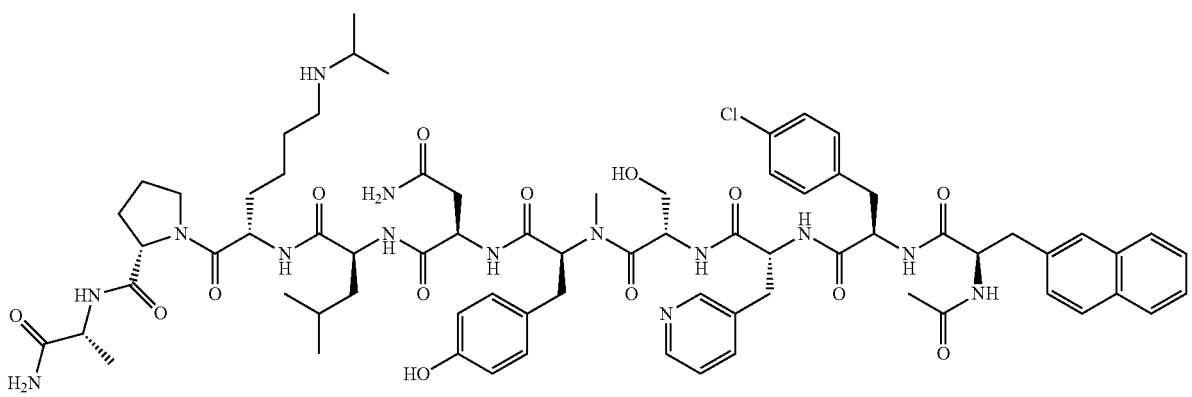 [SMILES: CC(=O)N[C@H](Cc1ccc2ccccc2c1)C(=O)N[C@H](Cc1ccc(Cl)cc1)C(=O)N[C@H](Cc1cccnc1)C(=O)N[C@@H](CO)C(=O)N(C)[C@@H](Cc1ccc(O)cc1)C(=O)N[C@H](CC(N)=O)C(=O)N[C@@H](CC(C)C)C(=O)N[C@@H](CCCCNC(C)C)C(=O)N1CCC[C@H]1C(=O)N[C@H](C)C(N)=O]

WO2010/029082 describes specific 2-carboxamide cycloamino urea derivatives which have been found to be highly selective for the alpha isoform of phosphatidylinositol-3-kinase. The compound (S)-Pyrrolidine-1,2-dicarbox- Abarelix can be prepared and formulated, e.g., as disclosed in U.S. Pat. No. 5,843,901.

Goserelin is disclosed in U.S. Pat. No. 4,100,274 and has the following chemical structure:

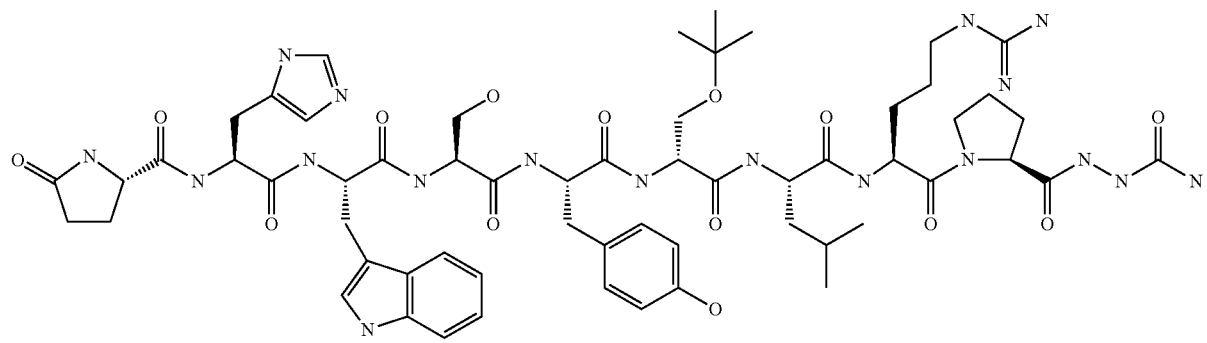 [SMILES: CC(C)C[C@H](NC(=O)[C@@H](COC(C)(C)C)NC(=O)[C@H](Cc1ccc(O)cc1)NC(=O)[C@H](CO)NC(=O)[C@H](Cc1c[nH]c2ccccc12)NC(=O)[C@H](Cc1cnc[nH]1)NC(=O)[C@@H]1CCC(=O)N1)C(=O)N[C@@H](CCCNC(=N)N)C(=O)N1CCC[C@H]1C(=O)NNC(N)=O]

Goserelin can be prepared and formulated, e.g., as disclosed in U.S. Pat. No. 4,100,274 or as marketed in the form of goserelin acetate, e.g., under the trademark ZOLADEX®.

Buserelin has the following chemical structure:

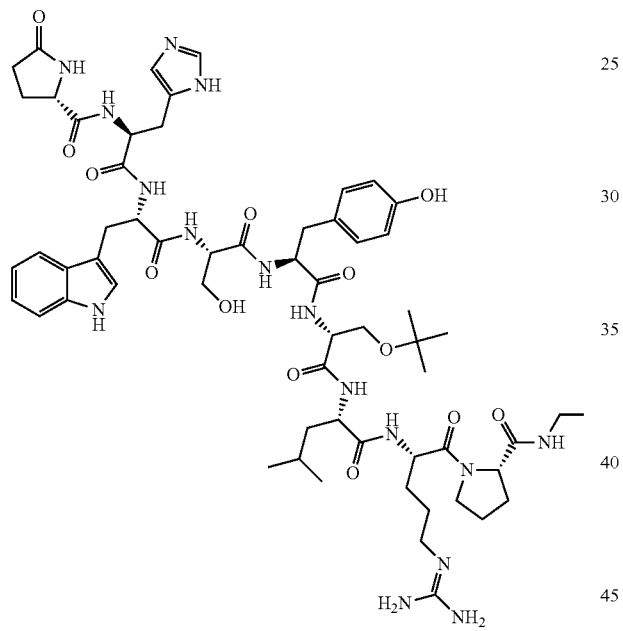

Buserelin can be formulated, e.g., as marketed, e.g., in the form of buserelin acetate under the trademark Suprefact®.

A preferred gonadorelin agonist for use in the present invention is goserelin or any pharmaceutically acceptable salt thereof. Most preferred, the gonadorelin agonist is goserelin acetate.

Antiestrogen agents are known in the art. The optional antiestrogen agent useful in the present invention include compounds which antagonizes the effect of estrogens at the estrogen receptor level.

Antiestrogen agents particularly useful in the present invention include, but is not limited to, tamoxifen, fulvestrant, raloxifene, raloxifene hydrochloride or any pharmaceutically acceptable salts thereof.

Tamoxifen has the following chemical structure:

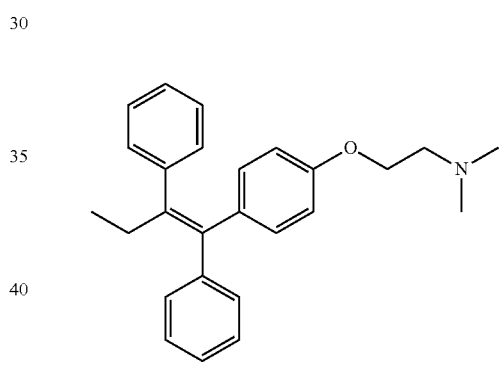

Tamoxifen can be administered, e.g., in the form as it is marketed in the form of tamoxifen citrate, e.g. under the trademark NOLVADEX® or SOLTAMOX®.

Fulvestrant is disclosed in U.S. Pat. No. 4,659,516 and has the following chemical structure:

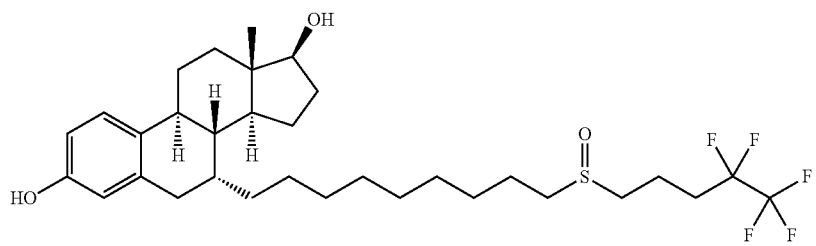

Fulvestrant can be prepared and formulated as disclosed in U.S. Pat. No. 4,659,516 or it can be administered, e.g., in the form as it is marketed, e.g. under the trademark FASLODEX®.

Raloxifene has the following chemical structure:

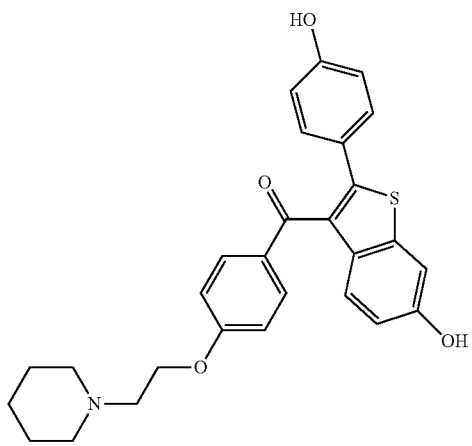 [SMILES: O=C(c1ccc(OCCN2CCCCC2)cc1)c1c(-c2ccc(O)cc2)sc2cc(O)ccc12]

Raloxifene can be administered, e.g, in the form of Raloxifene hydrochloride as it is marketed, e.g., under the trademark EVISTA®.

A preferred antiestrogen agent for use in the present invention is tamoxifen or any pharmaceutically acceptable salt thereof.

The structure of the active ingredients identified by code numbers, generic or trade names may be taken from the actual edition of the standard compendium "The Merck Index" or from databases, e.g., Patents International (e.g., IMS World Publications). The corresponding content thereof is hereby incorporated by reference.

Hereinafter, the dual pharmaceutical combination comprising (a) a PI3K inhibitor selected from COMPOUND A, COMPOUND B or any pharmaceutically acceptable salt thereof, and (b) a gonadorelin agonist and the triple combination comprising (a) a PI3K inhibitor selected from COMPOUND A, COMPOUND B or any pharmaceutically acceptable salt thereof, and (b) a gonadorelin agonist and (c) an antiestrogen agent will be referred to as a COMBINATION OF THE INVENTION.

In one embodiment, the COMBINATION OF THE INVENTION comprises (a) a PI3K inhibitor selected from COMPOUND A, COMPOUND B or any pharmaceutically acceptable salt thereof, and (b) a gonadorelin agonist selected from abarelix, goserelin, buserelin, or any pharmaceutically acceptable salts thereof.

In one embodiment, the COMBINATION OF THE INVENTION comprises (a) a PI3K inhibitor selected from COMPOUND A, COMPOUND B or any pharmaceutically acceptable salt thereof, and (b) a gonadorelin agonist selected from abarelix, goserelin, buserelin, or any pharmaceutically acceptable salts thereof, and (c) an antiestrogen agent selected from tamoxifen, fulvestrant, raloxifene, raloxifene hydrochloride or any pharmaceutically acceptable salts thereof.

In a preferred embodiment, the COMBINATION OF THE INVENTION is a dual pharmaceutical combination comprising (a) a PI3K inhibitor selected from COMPOUND A, COMPOUND B or any pharmaceutically acceptable salt thereof, and (b) goserelin or any pharmaceutically acceptable salt thereof or the triple pharmaceutical combination comprising (a) a PI3K inhibitor selected from COMPOUND A, COMPOUND B or any pharmaceutically acceptable salt thereof, and (b) goserelin or any pharmaceutically acceptable salt, and (c) tamoxifen or any pharmaceutically acceptable salt thereof.

Unless otherwise specified, or clearly indicated by the text, or not applicable, reference to therapeutic agents useful in the COMBINATION OF THE INVENTION includes both the free base of the compounds, and all pharmaceutically acceptable salts of the compounds.

Unless otherwise specified, or clearly indicated by the text, or not applicable, reference to therapeutic agents useful in the COMBINATION OF THE INVENTION further includes the additional embodiments wherein the PI3K inhibitor is specifically COMPOUND A or any of its pharmaceutically acceptable salts, and the embodiment wherein the PI3K inhibitor is specifically COMPOUND B or any of its pharmaceutically acceptable salts.

The present invention particularly pertains to a COMBINATION OF THE INVENTION useful for separate, simultaneous or sequential administration to a subject in need thereof for treating or preventing a cancer.

The present invention particularly pertains to a COMBINATION OF THE INVENTION useful for treating or preventing a cancer in a subject in need thereof. In one embodiment of the present invention, the COMBINATION OF THE INVENTION is used for the treatment or prevention of a cancer comprising administering to the subject a combination therapy, comprising an effective amount of a PI3K inhibitor selected from COMPOUND A, COMPOUND B, or any pharmaceutically acceptable salt thereof and an effective amount of a gonadorelin agonist (especially goserelin acetate). Preferably, these therapeutic agents are administered at therapeutically effective dosages which, when combined provide a beneficial effect. The administration may be separate, simultaneous or sequential.

In a further embodiment of the present invention, the COMBINATION OF THE INVENTION is used for the treatment or prevention of a cancer comprising administering to the subject a triple combination therapy, comprising an effective amount of a PI3K inhibitor selected from COMPOUND A, COMPOUND B, or any pharmaceutically acceptable salt thereof and an effective amount of a gonadorelin agonist (especially goserelin acetate) and an effective amount of an antiestrogen agent (especially tamoxifen). Preferably, these therapeutic agents are administered at therapeutically effective dosages which, when combined provide a beneficial effect. The administration may be separate, simultaneous or sequential.

The COMBINATION OF THE INVENTION is particularly useful for the treatment or prevention of a cancer in a subject in need thereof.

The term "cancer" is used herein to mean a broad spectrum of benign and malignant tumors, including all solid tumors and hematological malignancies. Examples of such tumors include but are not limited to benign or malignant tumors of the breast, lung (e.g., small-cell lung cancer and non-small cell lung cancer), bronchus, prostate, pancreas, colon, rectum, thyroid, liver and intrahepatic bile duct, hepatocellular, gastric, gastrointestine, glioma/glioblastoma, endometrial, melanoma, kidney (e.g., renal cell carcinoma) and renal pelvis, adrenal gland, bladder, uterus, cervix, ovary, esophagus, brain, head and neck, small intestine, multiple myeloma, leukemia (e.g., acute myelogenous leukemia, chronic myelogenous leukemia, lymphocytic leukemia, myeloid leukemia), non-Hodgkin lymphoma, villous colon adenoma, a neoplasia, a neoplasia of epithelial character and combinations thereof.

The COMBINATION OF THE INVENTION inhibits the growth of solid tumors, but also liquid tumors. In a further embodiment of the present invention, the cancer is a solid tumor. The term "solid tumor" especially means breast cancer, ovarian cancer, colon cancer, rectal cancer, gastro-intestinal cancer, cervix cancer, lung cancer (e.g., small-cell lung cancer and non-small cell lung cancer), kidney (e.g., renal cell carcinoma), melanoma, head and neck cancer, bladder cancer, and prostate cancer. Further, depending on the tumor type and particular combination used, a decrease of the tumor volume can be obtained. The COMBINATION OF THE INVENTION disclosed herein is also suited to prevent the metastatic spread of tumors and the growth or development of micrometastases. In a preferred embodiment, the COMBINATION OF THE INVENTION disclosed herein is used of the treatment of a cancer.

The COMBINATION OF THE INVENTION disclosed herein is suitable for the treatment of poor prognosis patients, especially such poor prognosis patients having a cancer which is resistant to treatment employing an antiestrogen agent as a sole therapeutic agent, e.g. a cancer of such patients who initially had responded to treatment with an antiestrogen agent and then relapsed. This cancer may have acquired resistance during prior treatment with one or more an antiestrogen agent, e.g., one of those listed above and incorporated herein by reference, e.g, tamoxifen. Thus, in one embodiment, the cancer is resistant to treatment employing an antiestrogen agent as a sole therapeutic agent.

In a further embodiment, the cancer is breast cancer or prostate cancer. In a preferred embodiment, the cancer is a hormone-receptor positive breast cancer or estrogen-receptor positive breast cancer.

Further, the COMBINATION OF THE INVENTION is particularly useful for the treatment or prevention of cancers having an overexpression or amplification of PI3K alpha, somatic mutation of PIK3CA or germline mutations or somatic mutation of PTEN or mutations and translocation of p85α that serve to up-regulate the p85-p110 complex.

In one embodiment, the present invention relates to the COMBINATION OF THE INVENTION for use in the treatment or prevention of a cancer.

In a further embodiment, the present invention relates to the COMBINATION OF THE INVENTION for use in the treatment or prevention of a breast cancer.

In a preferred embodiment, the present invention relates to a pharmaceutical combination comprising (a) a PI3K inhibitor selected from COMPOUND A, COMPOUND B or any pharmaceutically acceptable salt thereof, and (b) goserelin or any pharmaceutically acceptable salt thereof for use in the treatment or prevention of a hormone-receptor positive breast cancer.

In a preferred embodiment, the present invention relates to a pharmaceutical combination comprising (a) a PI3K inhibitor selected from COMPOUND A, COMPOUND B or any pharmaceutically acceptable salt thereof, and (b) goserelin or any pharmaceutically acceptable salt thereof, and (c) tamoxifen or any pharmaceutically acceptable salt thereof for use in the treatment or prevention of a hormone-receptor positive breast cancer.

In a further embodiment, the present invention relates to a COMBINATION OF THE INVENTION for use in the prevention of the metastatic spread of tumors or the growth or development of micrometastases in a subject in need thereof.

In one embodiment, the present invention relates to a method for treating or preventing a cancer, in a subject in need thereof comprising administering to said subject a therapeutically effective amount of a COMBINATION OF THE INVENTION. In each embodiment, COMBINATION OF THE INVENTION is preferably administered in a quantity that is jointly therapeutically effective for the treatment of said cancer in a patient suffering from said cancer.

In a further embodiment, the present invention relates to a method for treating or preventing a breast cancer, in a subject in need thereof comprising administering to said subject a jointly therapeutically effective amount of a COMBINATION OF THE INVENTION.

In a preferred embodiment, the present invention relates to a method for treating or preventing a hormone-receptor positive breast cancer in a subject in need thereof comprising administering to said subject a jointly therapeutically effective amount of (a) a PI3K inhibitor selected from COMPOUND A, COMPOUND B or any pharmaceutically acceptable salt thereof, and (b) goserelin or any pharmaceutically acceptable salt thereof.

In a preferred embodiment, the present invention relates to a method for treating or preventing a hormone-receptor positive breast cancer in a subject in need thereof comprising administering to said subject a jointly therapeutically effective amount of (a) a PI3K inhibitor selected from COMPOUND A, COMPOUND B or any pharmaceutically acceptable salt thereof, and (b) goserelin or any pharmaceutically acceptable salt thereof, and (c) tamoxifen or any pharmaceutically acceptable salt thereof.

In a further embodiment, the present invention relates to a method for preventing the metastatic spread of tumors or the growth or development of micrometastases in a subject in need thereof comprising simultaneously, separately or sequentially administering to said subject a jointly therapeutically effective amount of a COMBINATION OF THE INVENTION.

In one embodiment, the present invention relates to the use of a COMBINATION OF THE INVENTION for the preparation of a pharmaceutical composition or medicament for the treatment or prevention of a cancer.

In a further embodiment, the present invention relates to the use of a COMBINATION OF THE INVENTION for the preparation of a pharmaceutical composition or medicament for the treatment or prevention of a breast cancer.

In a preferred embodiment, the present invention relates to the use of a pharmaceutical combination comprising (a) a PI3K inhibitor selected from COMPOUND A, COMPOUND B or any pharmaceutically acceptable salt thereof, and (b) goserelin or any pharmaceutically acceptable salt thereof for the preparation of a pharmaceutical composition or medicament for the treatment or prevention of a hormone-receptor positive breast cancer.

In a preferred embodiment, the present invention relates to the use of a pharmaceutical combination comprising (a) a PI3K inhibitor selected from COMPOUND A, COMPOUND B or any pharmaceutically acceptable salt thereof, and (b) goserelin or any pharmaceutically acceptable salt thereof and (c) tamoxifen or any pharmaceutically acceptable salt thereof for the preparation of a pharmaceutical composition or medicament for the treatment or prevention of a hormone-receptor positive breast cancer.

In a further embodiment, the present invention relates to the use of a COMBINATION OF THE INVENTION for the preparation of a pharmaceutical composition or medicament for the prevention of the metastatic spread of tumors or the growth or development of micrometastases.

In one embodiment, the present invention relates to the use of the COMBINATION OF THE INVENTION for the treatment or prevention of a cancer.

In a further embodiment, the present invention relates to the use of a COMBINATION OF THE INVENTION for the treatment or prevention of a breast cancer.

In a preferred embodiment, the present invention relates to the use of a pharmaceutical combination comprising (a) a PI3K inhibitor selected from COMPOUND A, COMPOUND B or any pharmaceutically acceptable salt thereof, and (b) goserelin or any pharmaceutically acceptable salt thereof for the treatment or prevention of a hormone-receptor positive breast cancer.

In a preferred embodiment, the present invention relates to the use of a pharmaceutical combination comprising (a) a PI3K inhibitor selected from COMPOUND A, COMPOUND B or any pharmaceutically acceptable salt thereof, and (b) goserelin or any pharmaceutically acceptable salt thereof and (c) tamoxifen or any pharmaceutically acceptable salt thereof for the treatment or prevention of a hormone-receptor positive breast cancer.

In a further embodiment, the present invention relates to the use of a COMBINATION OF THE INVENTION for the prevention of the metastatic spread of tumors or the growth or development of micrometastases.

The nature of any cancer is multifactorial. Under certain circumstances, drugs with different mechanisms of action may be combined. However, just considering any combination of therapeutic agents having different mode of action does not necessarily lead to combinations with advantageous effects.

The administration of a COMBINATION OF THE INVENTION may result not only in a beneficial effect, e.g. a synergistic therapeutic effect, e.g, with regard to antiproliferative activity, e.g. with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the therapeutic agents used in the COMBINATION OF THE INVENTION.

A further benefit is that lower doses of the therapeutic agents of the COMBINATION OF THE INVENTION can be used, for example, that the dosages need not only often be smaller, but are also applied less frequently, or can be used in order to diminish the incidence of side-effects observed with one of the therapeutic agents alone. This is in accordance with the desires and requirements of the patients to be treated.

It can be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in an in vivo or in vitro test procedure as essentially described hereinafter.

Suitable clinical studies are in particular, for example, open label, randomized safety and efficacy studies in patients with a cancer. Such studies prove in particular the synergism of the therapeutic agents of the COMBINATION OF THE INVENTION. The beneficial effects on one or more cancers may be determined directly through the results of these studies which are known as such to a person skilled in the art. Such studies may be, in particular, be suitable to compare the effects of a monotherapy using either therapeutic agent and a COMBINATION OF THE INVENTION. In one embodiment, the dose of the PI3K inhibitor selected from COMPOUND A, COMPOUND B or a pharmaceutically acceptable salt thereof, is escalated until the Maximum Tolerated Dosage is reached, and the gonadorelin agonist is administered with a fixed dose. Alternatively, a PI3K inhibitor selected from COMPOUND A, COMPOUND B or a pharmaceutically acceptable salt thereof, may be administered in a fixed dose and the dose of the gonadorelin agonist may be escalated. Further, such studies may be, in particular, be suitable to compare the effects of a monotherapy or dual therapy to a triple pharmaceutical combination therapy of the present invention. In one embodiment, the dose of the phosphatidylinositol 3-kinase inhibitor selected from COMPOUND A, COMPOUND B or a pharmaceutically acceptable salt thereof, is administered and modified if needed to resolve side effects, and the gonadorelin agonist and the antiestrogen agent are administered at a fixed dose. For such studies, each patient may receive doses of the PI3K inhibitor either daily or intermittently. The efficacy of the treatment may be determined in such studies, e.g., after 8, 16, 24, 30, 36 weeks by evaluation of tumor growth or progression or symptom scores every 8 weeks, or e.g., after 8, 16, 24 weeks by evaluation of tumor growth or progression or symptom scores every 8 weeks until week 24 and then every 12 weeks until treatment end.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in one species can be predictive of the effect in other species and animal models exist, as described herein, to measure a synergistic effect and the results of such studies can also be used to predict effective dose ratio ranges and the absolute doses and plasma concentrations required in other species by the application of pharmacokinetic/pharmacodynamic methods. Established correlations between tumor models and effects seen in man suggest that synergy in animals may be demonstrated, for example, by xenograft models or in appropriate cell lines.

COMPOUND A is generally administered orally at a dose in the range from about 30 mg to about 300 mg, or about 60 mg to about 120 mg, or about 80 mg to about 100 mg, or about 100 mg per day in a human adult. Preferably, Compound A is administered orally at a dose of about 80 mg to about 100 mg per day in a human adult. The daily dose can be administered on a qd or bid schedule.

COMPOUND B is generally administered orally at a dose in the range from about 30 mg to about 450 mg, or about 100 mg to about 400 mg, or about 300 mg to about 400 mg, or about 250 mg to about 350 mg per day in a human adult. Preferably, COMPOUND B is administered orally at a dose of about 250 mg to about 350 mg per day in a human adult. The daily dose can be administered on a qd or bid schedule.

Goserelin may be administered at the suitable dose instructed by the prescribing information when used in the present combinations. However, dose reduction is also a possibility. In the present invention, goserelin may be administered to a human adult in the form of goserelin acetate by subcutaneous injection at a dose (equivalent to goserelin free base) in the range of about 2 mg to about 4 mg, or about 3 mg to about 4 mg, or preferably 3.6 mg every 28 days as, or by subcutaneous injection at a dose (equivalent to goserelin free base) in the range of about 9 mg to about 11 mg, about 10 mg to about 11 mg, or preferably 10.8 mg every 12 weeks. Preferably for the treatment of breast cancer, goserelin is administered at a dose (equivalent to goserelin free base) of 3.6 mg every 28 days.

Tamoxifen may be administered at the suitable dose instructed by the prescribing information when used in the present combinations. However, dose reduction is also a possibility. In the present invention, tamoxifen citrate may be orally administered at a dose (equivalent to tamoxifen free base) in the range of about 5 mg to about 25 mg, or about 10 mg to about 20 mg, or preferably 20 mg per day in a human adult.

It is understood that each therapeutic agent may be conveniently administered, for example, in one individual dosage unit or divided into multiple dosage units. It is further understood that that each therapeutic agent may be conveniently administered in doses once daily or doses up to four times a day.

In one embodiment, the present invention relates to a pharmaceutical composition or combined preparation comprising a quantity, which is jointly therapeutically effective against a cancer, of the COMBINATION OF THE INVENTION, and optionally at least one pharmaceutically acceptable carrier. In this pharmaceutical composition, the therapeutic agents PI3K inhibitor and/or the gonadorelin agonist and/or the antiestrogen agent can be administered in a single formulation or unit dosage form, administered concurrently but separately, or administered sequentially by any suitable route. Preferably, the PI3K inhibitor, the gonadorelin agonist and the antiestrogen agent are administered concurrently but separately.

When the gonadorelin agonist is goserelin or any pharmaceutically acceptable salt thereof (particularly goserelin acetate), it is typically separately administered by subcutaneous injection.

A therapeutically effective amount of the therapeutic agents of the COMBINATION OF THE INVENTION may be administered simultaneously or sequentially and in any order, and the components may be administered separately or as a fixed combination. For example, the method of treatment or prevention of a cancer, according to the invention may comprise (i) administration of the first therapeutic agent in free or pharmaceutically acceptable salt form and (ii) administration of the second therapeutic agent in free or pharmaceutically acceptable salt form, and, optionally, and (iii) administration of the third therapeutic agent in free or pharmaceutically acceptable salt form, separately, simultaneously or sequentially in any order, in jointly therapeutically effective amounts (preferably in synergistically effective amounts). The individual therapeutic agents of the COMBINATION OF THE INVENTION can be administered separately at different times during the course of therapy or concurrently in divided or single combination forms. The invention is therefore to be understood as embracing all such regimens of simultaneous or alternating treatment and the term "administering" is to be interpreted accordingly. Preferably, the PI3K inhibitor and the gonadorelin agonist and, if present, the antiestrogen agent are administered separately.

The effective dosage of each therapeutic agent employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single therapeutic agents required to alleviate, counter or arrest the progress of the condition.

The effective dosage of each of the therapeutic agents used in the COMBINATION OF THE INVENTION may require more frequent administration of one of the therapeutic agent(s) as compared to the other therapeutic agent(s) in the combination. Therefore, to permit appropriate dosing, packaged pharmaceutical products may contain one or more dosage forms that contain the combination of therapeutic agents, and one or more dosage forms that contain one of the combination of therapeutic agents, but not the other therapeutic agent(s) of the combination.

When any of the therapeutic agents employed in the COMBINATION OF THE INVENTION, are applied in the form as marketed as single drugs, their dosage and mode of administration can be in accordance with the information provided on the package insert of the respective marketed drug, if not mentioned herein otherwise.

The optimum ratios, individual and combined dosages, and concentrations of the therapeutic agents (a) and (b) employed in the COMBINATION OF THE INVENTION that yield efficacy without toxicity are based on the kinetics of the therapeutic agents' availability to target sites, and are determined using methods known to those of skill in the art The optimal dosage of each therapeutic agent for treatment or prevention of a cancer can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each therapeutic agent of the COMBINATION OF THE INVENTION that may be combined with the carrier materials to produce a single dosage form will vary depending upon the individual treated and the particular mode of administration. In some embodiments the unit dosage forms containing the combination of agents as described herein will contain the amounts of each therapeutic agent of the combination that are typically administered when the therapeutic agents are administered alone.

Frequency of dosage may vary depending on the therapeutic agent used and the particular condition to be treated or prevented. Patients may generally be monitored for therapeutic effectiveness using assays suitable for the condition being treated or prevented, which will be familiar to those of ordinary skill in the art.

The pharmaceutical composition according to the invention can be prepared in a manner known per se and are those suitable for enteral, such as oral or rectal, and parenteral administration to mammals (warm-blooded animals), including man. Alternatively, when the agents are administered separately, one can be an enteral formulation and the other can be administered parenterally.

Preferably, the pharmaceutical composition comprising the PI3K inhibitor COMPOUND A, COMPOUND B or any pharmaceutically acceptable salt thereof is suitable for enteral administration.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, sachets and furthermore ampoules. If not indicated otherwise, these are prepared in a manner known per se, for example by means of conventional mixing, granulating, sugar-coating, dissolving or lyophilizing processes. It will be appreciated that the unit content of one of the therapeutic agents contained in an individual dose of each dosage form need not in itself constitute an effective amount since the necessary effective amount can be reached by administration of a plurality of dosage units.

In preparing the compositions for oral dosage form, any of the usual pharmaceutically acceptable carriers may be employed, such as, for example, water, glycols, oils, alcohols, flavoring agents, preservatives, coloring agents; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed.

One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2003).

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

In a further embodiment, the present invention relates to a combined preparation comprising (a) one or more dosage units of a PI3K inhibitor selected from COMPOUND A, COMPOUND B or any pharmaceutically acceptable salt thereof and (b) one or more dosage units of a gonadorelin agonist for use in the treatment or prevention of a cancer.

In a further embodiment, the present invention relates to a combined preparation comprising (a) one or more dosage units of a PI3K inhibitor selected from COMPOUND A, COMPOUND B or any pharmaceutically acceptable salt thereof and (b) one or more dosage units of a gonadorelin agonist, and (c) one or more dosage units of an antiestrogen agent for use in the treatment or prevention of a cancer.

In one embodiment, the present invention provides a commercial package comprising as active ingredients of COMBINATION OF THE INVENTION and instructions for simultaneous, separate or sequential administration of said combination to a patient in need thereof for use in the treatment or prevention of a cancer.

In one embodiment, the present invention provides a commercial package comprising as active ingredient a phosphatidylinositol-3-kinase (PI3K) inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof, and instructions for simultaneous, separate or sequential administration of said active ingredient with a gonadorelin agonist to a patient in need thereof for use in the treatment or prevention of a cancer.

In a further embodiment, the present invention provides a commercial package comprising as active ingredient a PI3K inhibitor selected from 5-(2,6-di-morpholin-4-yl-pyrimidin-4-yl)-4-trifluoromethyl-pyridin-2-ylamine, (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof, and instructions for simultaneous, separate or sequential administration of said active ingredient with a gonadorelin agonist and an antiestrogen agent to a patient in need thereof for use in the treatment or prevention of a cancer.

The following Examples illustrate the invention described above; they are not, however, intended to limit the scope of the invention in any way. The beneficial effects of the pharmaceutical combination of the present invention can also be determined by the clinical study described below or other test models known as such to the person skilled in the pertinent art.

Example 1

A clinical study using (a) a phosphatidylinositol 3-kinase inhibitor COMPOUND A hydrochloride salt or COM- POUND B free base in combination with (b) goserelin acetate and (c) tamoxifen for treatment of premenopausal patients with hormone receptor-positive/HER2-negative locally advanced or metastatic breast cancer.

A randomized, open label, multi-center Phase II clinical trial of the combination comprising (a) a phosphatidylinositol 3-kinase inhibitor COMPOUND A hydrochloride salt or COMPOUND B free base in combination with (b) goserelin acetate and (c) tamoxifen is conducted in premenopausal patients with hormone receptor-positive/HER2-negative locally advanced or metastatic breast cancer. In the description below, the dosages provided are for COMPOUND A free base, but either COMPOUND A free base or its hydrochloride salt may be used.

In this study, the primary objective is to evaluate and compare the preliminary efficacy of (a) COMPOUND B in combination with tamoxifen and goserelin acetate (ARM 1) with tamoxifen and goserelin acetate (ARM 3), and (b) COMPOUND A in combination with tamoxifen and goserelin acetate (ARM 2) with tamoxifen and goserelin acetate (ARM 3). The primary endpoint is 9-month progression-free survival (PFS) rate (defined as the number of patients who have not progressed or died prior to 9 months from the date of randomization). The 9-month PFS rate is assessed based on local radiology assessments according to Response Evaluation Criteria in Solid Tumors (RECIST 1.1). In the absence of measurable disease at baseline, disease progression among patients with non-measurable lytic or mixed (lytic and blastic) bone lesions will be assessed based upon the appearance of one or more new lesions and progression of existing non-measurable lesions.

The secondary objectives include:
To evaluate and compare the efficacy of COMPOUND B/COMPOUND A in combination with tamoxifen plus goserelin vs tamoxifen plus goserelin, in terms of progression free survival (PFS).
To evaluate and compare the anti-tumor activity of COMPOUND B/COMPOUND A in combination with tamoxifen plus goserelin vs tamoxifen plus goserelin, in terms of overall response rate (ORR) and clinical benefit (CR+PR+SD).
To evaluate and compare the impact of COMPOUND B/COMPOUND A in combination with tamoxifen plus goserelin vs tamoxifen plus goserelin on patient-reported health status and impact on work.
To evaluate and compare the safety and tolerability of COMPOUND B/COMPOUND A in combination with tamoxifen plus goserelin vs tamoxifen plus goserelin in premenopausal hormone receptor-positive locally advanced and metastatic breast cancer patients, in terms of incidence, type, intensity, severity and seriousness of Adverse Events (AEs) and dose interruptions, reductions and dose intensity during the study.
To characterize the pharmacokinetics (PK) profile of oral COMPOUND B/COMPOUND A in combination with tamoxifen and goserelin, in addition to the characterization of tamoxifen itself to show that exposure of tamoxifen is comparable to control arm.

The secondary objectives are assessed based upon progression free survival (defined as the time from the date of randomization to the date of the first documented progressive disease or death due to any cause), overall response rate (defined as the proportion of patients with best overall response of complete response (CR) or partial response (PR) based on local investigator's assessment according to RECIST 1.1), and clinical benefit rate (defined as the proportion of patients with a best overall response of complete response (CR) or partial response (PR) or stable disease (SD) lasting more than 24 weeks based on local investigator's assessment). Analyses for secondary objectives is based on the full analysis set of all randomized patients.

Best overall response for each patient is determined from the sequence of overall (lesion) responses according to the following rules: (a) Complete Response (CR)=at least two determinations of CR at least 4 weeks apart before progression, (b) Partial Response (PR)=at least two determinations of PR or better at least 4 weeks apart before progression (and not qualifying for a CR), (c) Stable Disease (SD)=at least one SD assessment (or better)>5 weeks after randomization date (and not qualifying for CR or PR), (d) Progressive Disease (PD)=15 weeks after randomization date (and not qualifying for CR, PR or SD), and (e) UNK=all other cases (i.e. not qualifying for confirmed CR or PR and without SD after more than 6 weeks or early progression within the first 15 weeks).

Safety and tolerability are assessed by analysis of the following:
Incidence of adverse events (AEs) by grade, assessed according to the Common Terminology Criteria (CTCAE), version 4.03
Incidence of serious adverse events (SAEs), assessed according to the Common Terminology Criteria (CTCAE), version 4.03
Changes from baseline in laboratory results (hematology, blood chemistry, lipid profile, viral markers) qualifying as AEs
Changes from baseline in vital signs.
Severity assessment of potential mood alterations through Patient Health Questionnaire-9 (PHQ-9) and General Anxiety Disorder-7 (GAD-7), to be administered at screening to all patients and for follow up in patients randomized to ARM 2 only.

The eligibility of patients is determined during a screening period, which occurs within 1 to 21 days prior to treatment start. Eligible patients must provide a signed study Informed Consent Form prior to any screening procedure and be an adult female≥18 years of age on the day of consenting to the study. The following screening inclusion criteria is used:
1. Patient has histologically and/or cytologically confirmed diagnosis of breast cancer
2. Patient has radiological or objective evidence of inoperable locally advanced or metastatic breast cancer
3. Patient has HER2-negative breast cancer (based on most recently analyzed tumor sample) defined as a negative immunohistochemistry (IHC), fluorescent, non-florescent chromogenic or silver in situ hybridization (respectively FISH/CISH/SISH) test or an IHC status of 0, 1+ or 2+ (if IHC 2+, a negative SISH/FISH/CISH test is required) by local laboratory approved testing
4. Patient has estrogen-receptor (ER) positive and/or progesterone-receptor (PgR) positive breast cancer by local laboratory testing
5. Patient is premenopausal. Premenopausal status is defined as either:
   a) patient had last menstrual period within the last 12 months,
   OR
   b) if on tamoxifen within the past 3 months, with a plasma estradiol≥1.0 pg/mL and FSH≤40 IU/l or in the premenopausal range, according to local laboratory definition, OR
  c) in case of chemotherapy induced amenorrhea, with a plasma estradiol≥1.0 pg/mL and/or FSH≤40 IU/l or in the premenopausal range according to local laboratory definition.
6. Patients agreed to use effective contraception or not be of childbearing potential.
7. Patient has no previous history of endocrine therapy in the metastatic setting. However,
  Patients who received endocrine therapy with duration less than 3 weeks and discontinued for a reason other than suspicious or evidence of disease progression are eligible
  Adjuvant treatment with tamoxifen is allowed. In this setting, prior use of LH-RH agonist/antagonist is permitted only if disease recurrence occurred after at least 12 months of last dose of LH-RH agonist/antagonist was received.
  Patients who were already established on bisphosphonate therapy may continue on bisphosphonates.
8. Patient has received prior chemotherapy line for metastatic breast cancer.
9. For patient who received prior systemic therapy, radiological or objective evidence of recurrence or progression on or after the last systemic therapy is needed
10. Patient must have:
  measurable disease as per RECIST 1.1 (including lytic or mixed (lytic+blastic) bone lesions, with an identifiable soft tissue component that meets the measurability criteria per RECIST 1.1, or
  non-measurable lytic or mixed (lytic+blastic) bone lesions in the absence of measurable disease.
11. Patient has adequate bone marrow and organ function as defined by the following laboratory values:
  Absolute Neutrophil Count (ANC)≥1.0×10$^9$/L
  Platelets (PLT)≥100×10$^9$/L
  Hemoglobin (Hgb)≥9 g/dl
  International normalized ratio (INR)≤1.5
  Potassium, calcium (corrected for serum albumin) and magnesium within normal limits (WNL) for the institution
  Serum creatinine≤1.5× Upper Limit of Normal (ULN)
  Alanine aminotransferase (AST) and aspartate aminotransferase (ALT)≤ULN (or <3.0×ULN if liver metastases are present)
  Total serum bilirubin≤ULN (or <1.5×ULN if liver metastases are present; or total bilirubin<3.0×ULN with direct bilirubin within normal range in patients with well documented Gilbert's Syndrome, which is defined as presence of several episodes of unconjugated hyperbilirubinemia with normal results from CBC count [including normal reticulocyte count and blood smear], normal liver function test results, and absence of other contributing disease processes at the time of diagnosis [see Appendix 1])
  Fasting plasma glucose<120 mg/dL or 6.7 mmol/L
  HbA1c<8%
12. Patient has an Eastern Cooperative Oncology Group (ECOG) performance status≤2 which the investigator believes is stable at the time of screening.
13. Patient has negative serum pregnancy test (β-hCG) within 72 hrs before starting study treatment.
14. Patient is able to swallow and retain oral medication
Patients must meet all screening inclusion criteria to be eligible. The following screening exclusion criteria is used:

1. Patient is post-menopausal.
2. Women of child-bearing potential (defined as: all women physiologically capable of becoming pregnant), unless they are using effective methods of contraception during dosing of study treatment. Effective contraception methods include:
  Total abstinence (when this is in line with the preferred and usual lifestyle of the subject. Periodic abstinence (e.g., calendar, ovulation, symptothermal, post-ovulation methods) and withdrawal are not acceptable methods of contraception
  Have had or tubal ligation at least six weeks before taking study treatment.
  Male sterilization (at least 6 months prior to screening). For female subjects on the study the vasectomized male partner should be the sole partner for that subject
  Barrier methods of contraception: Condom or Occlusive cap (diaphragm or cervical/vault caps) with spermicidal foam/gel/film/cream/vaginal suppository
  Placement of an intrauterine device (IUD) or intrauterine system (IUS)
  Oral contraceptives (OC), injected or implanted hormonal methods are not allowed as the sole method of contraception.
3. Patient is pregnant or lactating, wherein pregnancy is defined as the state of a female after conception and until the termination of gestation, confirmed by a positive human chorionic gonadotrophin (hCG) laboratory test.
4. Patient has received previous endocrine treatments in the metastatic setting.
5. Patient has received previous treatment with PI3K inhibitors, AKT inhibitors, and/or mTOR inhibitors
6. Patient has received more than one chemotherapy line for metastatic disease
  A chemotherapy line in advanced disease is an anticancer regimen that contains at least 1 cytotoxic chemotherapy agent and was discontinued due to progression. If a cytotoxic chemotherapy regimen was discontinued for a reason other than disease progression then this regimen does not count as a "prior line of chemotherapy"
  Adjuvant/neo-adjuvant therapy will be counted as prior line of chemotherapy for metastatic/recurrent disease if the patient had a progression/recurrence while or within 6 months after completion of the therapy (12 months for taxane-based therapy)
7. Patient has a known hypersensitivity to any of the excipients of COMPOUND A, COMPOUND B, tamoxifen or goserelin acetate.
8. Patient has symptomatic CNS metastases.
  Patients with asymptomatic CNS metastases may participate in this trial. The patient must have completed any prior local treatment for CNS metastases≥28 days prior to the entry (including radiotherapy and/or surgery)
9. Patient has a concurrent malignancy or malignancy within 3 years of study enrollment (with the exception of adequately treated, basal or squamous cell carcinoma, nonmelanomatous skin cancer or curatively resected cervical cancer).
10. Patient who has received wide field radiotherapy≤4 weeks or limited field radiation for palliation≤2 weeks prior to starting study drug or who have not recovered to grade 1 or better from related side effects of such therapy (with exception of alopecia alopecia).
11. Patient has not recovered to grade 1 or better (except alopecia) from related side effects of any prior antineoplastic therapy.

12. Patient has had major surgery within 14 days prior to starting study drug or has not recovered from major side effects.
13. Patient is currently receiving increasing or chronic treatment (>5 days) with corticosteroids or another immunosuppressive agent, as chronic administration of corticosteroids (>5 days) can induce CYP3A4.
    The following uses of corticosteroids are permitted: single doses; topical applications (e.g., rash), inhaled sprays (e.g., obstructive airways diseases), eye drops or local injections (e.g., intra-articular)
14. Patient is currently receiving warfarin or other coumarin derived anti-coagulant, for treatment, prophylaxis or otherwise. Therapy with heparin, low molecular weight heparin (LMWH), or fondaparinux is allowed.
15. Patient is currently receiving treatment with drugs known to be moderate or strong inhibitors or inducers of isoenzyme CYP3A. The patient must have discontinued strong inducers for at least one week and must have discontinued strong inhibitors before the treatment phase is initiated. Switching to a different medication prior to entry in the treatment phase is allowed. Please refer to the Table 14-1 in Appendix 2 for a list of strong and moderate inhibitors and inducers of CYP3A4.
16. Patient has a score≥12 on the Patient Health Questionnaire-9 (PHQ-9).
17. Patient selects a response of "1, 2 or 3" to question number 9 on the PHQ-9 questionnaire regarding potential for suicidal thoughts or ideation (independent of the total score of the PHQ-9).
18. Patient has a General Anxiety Disorder-7 (GAD-7) mood scale score≥15.
19. Patient has a medically documented history of or active major depressive episode, bipolar disorder (I or II), obsessive-compulsive disorder, schizophrenia, a history of suicidal attempt or ideation, or homicidal ideation (e.g. risk of doing harm to self or others) or patients with active severe personality disorders (defined according to DSM-IV) are not eligible. Note: for patients with psychotropic treatments ongoing at baseline, the dose and the schedule should not be modified within the previous 6 weeks prior to start of study drugs.
20. Patient has ≥Common Terminology Criteria for Adverse Events (CTCAE) grade 3 anxiety.
21. Patient has active cardiac disease or a history of cardiac dysfunction including any of the following:
    a. Unstable angina pectoris within 6 months prior to study entry
    b. Symptomatic pericarditis
    c. Documented myocardial infarction within 6 months prior to study entry
    d. History of documented congestive heart failure (New York Heart Association functional classification III-IV)
    e. Documented cardiomyopathy
    f. Uncontrolled hypertension.
22. Patient has a Left Ventricular Ejection Fraction (LVEF) <50% as determined by Multiple Gated acquisition (MUGA) scan or echocardiogram (ECHO).
23. Patient has any of the following cardiac conduction abnormalities
    a. Ventricular arrhythmias except for benign premature ventricular contractions
    b. Supraventricular and nodal arrhythmias requiring a pacemaker or not controlled with medication
    c. Conduction abnormality requiring a pacemaker
    d. Other cardiac arrhythmia not controlled with medication
    e. Patient has a QTcF>480 msec on the screening ECG (using the QTcF formula)
24. Patient is currently receiving treatment with medication that has a known risk to prolong the QT interval or inducing Torsades de Pointes, and the treatment cannot be discontinued or switched to a different medication prior to randomization.
25. Patient has impairment of GI function or GI disease that may significantly alter the absorption of COMPOUND A or COMPOUND B (e.g., ulcerative diseases, uncontrolled nausea, vomiting, diarrhea, malabsorption syndrome, or small bowel resection).
26. Patient has any other concurrent severe and/or uncontrolled medical condition that would, in the investigator's judgment contraindicate patient participation in the clinical study (e.g. chronic pancreatitis, chronic active hepatitis, etc.).
27. Patient has a history of non-compliance to medical regimen or inability to grant consent.
28. Patient has a known history of HIV infection (testing not mandatory)
29. Patient is concurrently using other approved or investigational antineoplastic agent.
30. Patient has participated in a prior investigational study within 30 days prior to enrollment or within 5-half lives of the investigational product, whichever is longer.

Patients must not meet any of the screening exclusion criteria to be eligible for the study.

The PHQ-9 and GAD-7 are validated (Kroenke, J. Gen Intern. Med. 16(9):606-13 (September 2001), Spitzer et al., Arch. Intern. Med. 166(10):1092-7 (May 22, 2006), and Spitzer et al, JAMA 282(18): 1737-44 (Nov. 10, 1999)), patient-self administered questionnaires developed for use in clinical practices. Both questionnaires must be completed during screening.

Patients may voluntarily withdraw from the study treatment or be removed at the investigator's decision. Patients must be withdrawn from the study treatment for reasons of death or pregnancy. Patients may be withdrawn from the study if any of the following occur: adverse event, lost to follow-up, non-compliance with study treatment, physician decision, progressive disease, protocol deviation, pregnancy, or discovery of failure of randomization.

After screening, patients are randomized into one (1) of the following three (3) treatment arms in a ratio of 1:1:1— ARM 1: COMPOUND B in combination with goserelin acetate and tamoxifen, ARM 2: COMPOUND A in combination with goserelin acetate and tamoxifen, and ARM 3: Combination of goserelin acetate and tamoxifen. Randomization is stratified by: (a) liver and/or lung disease (present or absent), and (b) previous treatment with tamoxifen (present or absent). To ensure that randomization is unbiased and concealed from patients and investigators, randomization is conducted by the Interactive Response Technology (IRT) provider using a validated system that automates the random assignment of patient numbers to randomization numbers. These randomization numbers are linked to different treatment arms, which are in turn linked to medication numbers. A separate medication randomization list is produced by the vendor to assign random medication numbers to medication packs containing each study drug. Approximately 50-70 patients are enrolled in each study arm, preferably about 64 patients in each arm.

Patients are administered the study drugs designated to their assigned treatment arm. COMPOUND A is administered orally at a dosage of 100 mg once daily on a continuous dosing schedule starting on day 1. COMPOUND B is administered orally at a dosage of 350 mg once daily on a continuous dosing schedule starting on day 1. Tamoxifen is administered orally at a dosage of 20 mg once daily on a continuous dosing schedule. Goserelin acetate is administered at a dose of 3.6 mg subcutaneous on day 1 cycle 1 and every 28 days. In the study, one treatment cycle is 28 days.

Dose modifications are allowed for COMPOUND A and COMPOUND B only. No dose modification is allowed for tamoxifen or goserelin acetate. For each patient, a maximum of 2 dose modifications are allowed after which the patient is held from treatment with COMPOUND A or COMPOUND B. For COMPOUND A, the starting dose of 100 mg/day may be reduced to 80 mg/day and then 60 mg/day. For COMPOUND B, the starting dose of 350 mg/day may be reduced to 300 mg/day and then 250 mg/day. If treatment with COMPOUND A or COMPOUND B is held for more than 28 days, the patient must be permanently discontinued.

Guidelines for dose modification and dose interruption of COMPOUND A or COMPOUND B are described in the following table (Table 1-1):

| Worst toxicity (CTCAE 4.03 Grade)** | Dose Modifications for COMPOUND B/COMPOUND A |
|---|---|
| HEMATOLOGICAL | |
| Neutropenia (ANC) | |
| Grade 1 (ANC < LLN-1.5 × $10^9$/L) | Maintain dose level |
| Grade 2 (ANC < 1.5-1.0 × $10^9$/L) | |
| Grade 3 (ANC < 1.0-0.5 × $10^9$/L) | Omit dose until resolved to ≤ Grade 1, then: |
| Grade 4 (ANC < 0.5 × $10^9$/L) | If resolved in ≤7 days, then maintain dose level |
| | If resolved in >7 days, then ↓ 1 dose level |
| Febrile neutropenia (ANC < 1.0 × $10^9$/L, with a single temperature of ≥38.3° C. or a sustained temperature of ≥38° C. for more than one hour) | Omit dose until resolved, then ↓ 1 dose level |
| Thrombocytopenia | |
| Grade 1 (PLT < LLN-75 × $10^9$/L) | Maintain dose level |
| Grade 2 (PLT < 75-50 × $10^9$/L) | |
| Grade 3 (PLT < 50-25 × $10^9$/L) | Omit dose until resolved to ≤ Grade 1, then: |
| | If resolved in ≤7 days, then maintain dose level |
| | If resolved in >7 days, then ↓ 1 dose level |
| Grade 4 (PLT < 25 × $10^9$/L) | Omit dose until resolved to ≤ Grade 1, then ↓ 1 dose level |
| RENAL | |
| Serum creatinine | |
| <2 × ULN | Maintain dose level |
| 2-3 × ULN | Omit dose until resolved to ≤ grade 1, then: |
| | If resolved in ≤7 days, then maintain dose level |
| | If resolved in >7 days, then ↓ 1 dose level |
| Grade 3 (>3.0-6.0 × ULN) | Permanently discontinue patient from COMPOUND B/COMPOUND A |
| Grade 4 (>6.0 × ULN) | Permanently discontinue patient from COMPOUND B/COMPOUND A |
| HEPATIC | |
| Bilirubin | |
| (*for patients with Gilbert Syndrome these dose modifications apply to changes in direct bilirubin only) | |
| Same grade as baseline (i.e. Grade 0 or Grade 1 if presence of liver metastasis) | Maintain dose level with LFTs* monitored per protocol |
| Increase from baseline Grade 0 to >1.5 ULN or from baseline Grade 1 to Grade 2 | ↓ 1 dose level |
| Increase of two grades from baseline (from baseline Grade 0 to Grade 2 or from baseline Grade 1 to Grade 3) | Omit dose until resolved to Grade 1 or less, then ↓1 dose level. If not recovery in ≤28 days, discontinue permanently |
| Grade 4 (>20.0 × ULN) | Discontinue permanently COMPOUND B/COMPOUND A |
| AST or ALT without bilirubin elevation >2 ULN | |
| Note: confounding factors and/or alternative causes for increased transaminases like concomitant medications, infection, hepato-biliary disorder, obstruction, liver metastasis, etc should be excluded before dose interruption/reduction | |
| Grade 1 (>ULN-3.0 × ULN) | Maintain dose level with LFTs* monitored per protocol |
| Grade 2 (>3.0-5.0 × ULN) without total bilirubin elevation to >2.0 × ULN | Omit dose until resolved to ≤ Grade 1, then |
| | If resolved in ≤7 days, then maintain dose level |
| | If resolved in >7 days, then ↓ 1 dose level |
| Grade 3 (>5.0-20.0 × ULN) without total bilirubin elevation to >2.0 × ULN | Omit dose until resolved to ≤ Grade 1, then |
| | If resolved in ≤7 days, then maintain dose level |
| | If resolved in >7 days, then ↓ 1 dose level |
| Grade 4 (>20.0 × ULN) without bilirubin elevation to >2.0 × ULN | Omit dose until resolved to ≤ Grade 1, then ↓ 1 dose level |
| AST or ALT and concurrent Bilirubin | |
| AST or ALT >3.0 × ULN and total bilirubin >2.0 × ULN | Permanently discontinue COMPOUND B/COMPOUND A |

*(LFTs include albumin, ALT, AST, total bilirubin (fractionated if total bilirubin >2.0 × ULN), alkaline phosphatase (fractionated if alkaline phosphatase is grade 2 or higher) and GGT)
Hepatic toxicity monitoring (*for patients with Gilbert Syndrome: total and direct bilirubin must be monitored, intensified monitoring applies to changes in direct bilirubin only; the monitoring includes the following LFTs:

| Worst toxicity (CTCAE 4.03 Grade)** | Dose Modifications for COMPOUND B/COMPOUND A |
|---|---| albumin, ALT, AST, total bilirubin (fractionated if total bilirubin >2.0 × ULN), alkaline phosphatase (fractionated if alkaline phosphatase is grade 2 or higher) and GGT):
Cycle 1 and 2: every other week (if visit schedule allows a more frequent monitoring this should be considered) or more frequently if clinically indicated especially for patients with borderline acceptable AST/ALT/bilirubin* values
Cycle 3 and onward: monthly or more frequently if clinically indicated
In case of any occurrence of ALT/AST/bilirubin* increase ≥ grade 2 the liver function tests must be monitored weekly or more frequently if clinically indicated until resolved to ≤ grade 1
In case of any occurrence of ALT/AST/bilirubin* increase ≥ grade 3 the liver function tests must be monitored weekly or more frequently if clinically indicated until resolved to ≤ grade 1; hereafter the monitoring should be continued every other week or more frequently if clinically indicated until the end of treatment with study medication
Patients who discontinued study treatment should be monitored weekly, including LFTs* or more frequently if clinically indicated until resolved to ≤ grade 1 or stabilization (no CTCAE grade change over 4 weeks).

ENDOCRINE/METABOLIC
Fasting Plasma Glucose (FPG)

| | |
|---|---|
| Grade 1 (>ULN-160 mg/dL) [>ULN-8.9 mmol/L] | Maintain dose level, check FPG every week<br>initiate or intensify medication with appropriate antidiabetic treatment as per investigator's discretion<br>instruct patient to follow dietary guidelines according to local and/or institutional standards for management of diabetes mellitus (such as those provided by the American Diabetes Association) during the study<br>consider use of oral anti-hyperglycemic therapy such as metformin (or intensify existing medications)<br>check FPG at least weekly for 8 weeks, then continue checking at least every 2 weeks |
| Grade 2 (>160-250 mg/dL) [>8.9-13.9 mmol/L] | If signs or symptoms of hyperglycemia (for example, mental status changes, excessive thirst, polyuria), omit COMPOUND B/COMPOUND A immediately and manage as for Grade 3 hyperglycemia (see below)<br>If asymptomatic, maintain dose and re-check FPG within 24 hours. If grade worsens or improves then follow specific grade recommendations. If FPG remains at Grade 2:<br>maintain dose level and monitor FPG at least weekly until FPG resolves to ≤ Grade 1<br>initiate or intensify medication with appropriate antidiabetic treatment such as metformin; consider adding a second oral agent if no improvement after several days<br>as instruct patient to follow dietary guidelines according to local and/or institutional standards for management of diabetes mellitus (such those provided by the American Diabetes Association) during the study<br>If FPG does not resolve to ≤ Grade 1 within 14 days after institution of appropriate anti-diabetic treatment reduce COMPOUND B/COMPOUND A by 1 dose level<br>Continue with anti-diabetic treatment and check FPG at least weekly for 8 weeks, then continue checking at least every 2 weeks |
| Grade 3 (>250-500 mg/dL) [>13.9-27.8 mmol/L] | Immediately omit COMPOUND B/COMPOUND A, initiate or intensify medication with appropriate anti-diabetic treatment, re-check FPG within 24 hours. If grade worsens or improves then follow specific grade recommendations.<br>If FPG remains at Grade 3:<br>administer intravenous hydration and intervention for electrolyte/ketoacidosis/hyperosmolar disturbances as clinically appropriate<br>continue to omit COMPOUND B/COMPOUND A monitor FPG at least twice weekly until FPG resolves to ≤ Grade 1<br>If FPG resolves to ≤ Grade 1 in 7 days or less, then re-start COMPOUND B/COMPOUND A and ↓ 1 dose level<br>If FPG remains greater than Grade 1 severity for more than 7 days, then discontinue patient from COMPOUND B/COMPOUND A<br>initiate or continue anti-diabetic treatment as appropriate<br>instruct patient to follow dietary guidelines according to local and/or institutional standards for management of diabetes mellitus (such as those provided by the American Diabetes Association) during the study<br>consider use of oral anti-hyperglycemic therapy such as metformin<br>check FPG at least weekly for 8 weeks, then continue checking at least every 2 weeks<br>For non-fasting plasma glucose >250-500 mg/dL (>13.9-27.8 |

-continued

| Worst toxicity (CTCAE 4.03 Grade)** | Dose Modifications for COMPOUND B/COMPOUND A |
|---|---|
| | mmol/L) accompanied by signs/symptoms of hyperglycemia (for example, mental status changes, excessive thirst, polyuria), or presence of blood or urine ketones, omit COMPOUND B/ COMPOUND A and following guidance for management of Grade 3 fasting plasma glucose (FPG) |
| Grade 4 (>500 mg/dL) [≥27.8 mmol/L] | Immediately omit COMPOUND B/COMPOUND A, initiate or intensify medication with appropriate anti-diabetic treatment, re-check within 24 hours. if grade improves then follow specific grade recommendations. |
| | If FPG is confirmed at Grade 4: |
| | administer intravenous hydration and intervention for electrolyte/ketoacidosis/hyperosmolar disturbances as clinically appropriate, |
| | discontinue patient from COMPOUND B/COMPOUND A, |
| | instruct patient to follow dietary guidelines according to local and/or institutional standards for management of diabetes mellitus (such as those provided by the American Diabetes Association) during the study, |
| | consider use of oral anti-hyperglycemic therapy such as metformin check FPG at least weekly for 8 weeks, then continue checking at least every 2 weeks if clinically indicated |
| | For non-fasting plasma glucose >500 mg/dL (>27.8 mmol/L) accompanied by signs/symptoms of hyperglycemia (for example, mental status changes, excessive thirst, polyuria), or presence of blood or urine ketones, discontinue COMPOUND B/COMPOUND A and following guidance for management of Grade 4 fasting plasma glucose (FPG). |

CARDIAC

Cardiac - Left Ventricular systolic dysfunction

| | |
|---|---|
| Asymptomatic, resting ejection fraction 40-50%; or 10-20% drop from baseline | Maintain dose level, and continue COMPOUND B/COMPOUND A with caution Repeat LVEF within 4 weeks or as clinically appropriate |
| Symptomatic, responsive to intervention, ejection fraction 20-39% or >20% drop from baseline | Omit COMPOUND B/COMPOUND A until resolved* (as defined below), then ↓ 1 dose level LVEF measurement to be repeated, if not resolved* within 28 days, permanently discontinue patient from COMPOUND A treatment |
| Refractory or poorly controlled, ejection fraction <20% | Permanently discontinue patient from COMPOUND B/ COMPOUND A |

*the event is considered resolved when the patient is asymptomatic, has a resting ejection fraction ≥40% and ≤20% decrease from baseline.

Cardiac - QTc prolongation

| | |
|---|---|
| QTcF >500 ms (≥Grade 3) or >60 ms change from baseline on at least two separate ECGs | First Occurrence: Omit COMPOUND B/COMPOUND A Perform an analysis of serum potassium and magnesium, and if below lower limit of normal, correct with supplements to within normal limits. Concomitant medication usage must be reviewed. Perform a repeat ECG within one hour of the first QTcF of >500 ms or >60 ms from baseline If QTcF remains >500 ms or >60 ms from baseline, repeat ECG as clinically indicated, but at least once a day until the QTcF returns to <480 ms. Seek cardiologist input. Once QTcF prolongation has resolved, COMPOUND B/ COMPOUND A may be restarted at a one lower dose level Second Occurrence: Permanently discontinue patient from COMPOUND B/ COMPOUND A |

Other Cardiac Events

| | |
|---|---|
| Grade 1 or 2 | Maintain dose level |
| Grade 3 | Omit dose until resolved to ≤ Grade 1, then ↓ 1 dose level |
| Grade 4 | Permanently discontinue patient from COMPOUND B/ COMPOUND A |

OTHER

Mood alteration

| | |
|---|---|
| Grade 1* | Maintain dose level Consider psychiatric consultation at the investigator's discretion and introduce optimal management |
| Grade 2* | Omit dose until resolved to ≤ Grade 1 or baseline status Consider psychiatric consultation at the investigator's discretion and introduce optimal management First event: if the condition resolved to Grade ≤ 1 or to baseline status, continue to co-medicate and then maintain the dose level Second and further events: if the condition resolved to Grade ≤ 1 or to baseline status, continue to co-medicate and then ↓ 1 dose level |

-continued

| Worst toxicity (CTCAE 4.03 Grade)** | Dose Modifications for COMPOUND B/COMPOUND A |
|---|---|
| Grade 3* | Omit dose until resolved to ≤ Grade 1 or baseline status<br>Psychiatric consultation is required and introduce optimal management<br>If the condition resolved to Grade ≤1 or to baseline status, continue to co-medicate and then ↓ 1 dose level |
| Grade 4* | Permanently discontinue patient from COMPOUND B/COMPOUND A<br>Psychiatric consultation is required and introduce optimal management |

*Note: For patients randomized to Arm2 (COMPOUND A), for all grades, if question 9 on the PHQ-9 has a positive response (as indicated by selecting "1", "2", or "3"), omit study drug and refer patient for psychiatric consult regardless of the total questionnaire score or CTCAE grading to confirm if study drug should be interrupted or permanently discontinued.

| | Rash |
|---|---|
| Grade 1 | Maintain dose level. Consider to initiate appropriate skin toxicity therapy (such as antihistamines, topical corticosteroids) |
| Grade 2 | First occurrence: Omit dose until resolved to grade ≤1 then:<br>If resolved in ≤2 weeks, maintain dose level.<br>If resolved in more than 2 weeks, ↓ 1 dose level.<br>Second occurrence: ↓ 1 dose level.<br>Initiate/intensify appropriate skin toxicity therapy (such as antihistamines, topical corticosteroids) |
| Grade 3 | First occurrence: omit dose until resolved to CTCAE Grade ≤1; then ↓1 dose level.<br>Second occurrence: permanently discontinue patient from COMPOUND B/COMPOUND A. If skin rash is readily manageable, reintroduction at a lower dose level might be considered at the discretion of the investigator.<br>According to the investigators discretion, a paired skin biopsy could be obtained (from both an affected and an unaffected skin area for local histopathology assessment) if clinically appropriate. |
| Grade 4 | Permanently discontinue patient from COMPOUND B/COMPOUND A |
| | Fatigue (asthenia) |
| Grade 1 or 2 | Maintain dose level |
| Grade 3 | Omit dose until resolved to ≤ Grade 1, then:<br>If resolved in ≤7 days, maintain dose level<br>If resolved in >7 days, ↓ 1 dose level |
| Grade 4 | Permanently discontinue patient from COMPOUND B/COMPOUND A |
| Pneumonitis | See table 1-2 |
| | Other non- hematological adverse events |
| Grade 1 or 2 | Maintain dose level |
| Grade 3 | Omit dose until resolved to ≤ Grade 1, then ↓ 1 dose level |
| Grade 4 | Permanently discontinue patient from COMPOUND B/COMPOUND A<br>Note: Omit dose for ≥ Grade 3 vomiting or Grade 3 nausea only if the vomiting or nausea cannot be controlled with optimal antiemetic |
| | Stomatitis/Oral mucositis |
| Grade 1/Tolerable Grade 2 | Maintain dose level.<br>Non-alcoholic or salt water mouth wash |
| Intolerable Grade 2 or Grade 3 | First occurrence: hold until ≤ G1 and ↓ 1 dose level (if stomatitis is readily manageable with optimal management, re-introduction at the same level might be considered at the discretion of the investigator).<br>Second occurrence: hold until ≤ G1 and ↓ 1 dose level. |
| Grade 4 | Permanently discontinue patient from COMPOUND B/COMPOUND A |

**Common Terminology Criteria for Adverse Events (CTCAE) version 4.03.

For pneumonitis, the following guidelines are followed:

| Worst Grade Pneumonitis | Required Investigations | Management of Pneumonitis | COMPOUND B/COMPOUND A dose Adjustments |
|---|---|---|---|
| Grade 1 | CT scans with lung windows. Repeat at least every 8 weeks until return to within normal limits. | No specific therapy is required | Administer 100% of COMPOUND B/COMPOUND A dose. |
| Grade 2 | CT scan with lung windows. Consider pulmonary function | Symptomatic only. Consider | Reduce COMPOUND B/COMPOUND A dose by 1 dose |

| Worst Grade Pneumonitis | Required Investigations | Management of Pneumonitis | COMPOUND B/COMPOUND A dose Adjustments |
|---|---|---|---|
| | testing includes: spirometry, DLCO, and room air O2 saturation at rest. Repeat at least every 8 weeks until return to within normal limits. Consider a bronchoscopy with biopsy and/or BAL. | corticosteroids if symptoms are troublesome. | level until recovery to < Grade 1. Study treatment may also be interrupted if symptoms are troublesome. Patients will discontinue study treatment if they fail to recover to < Grade 1 within 28 days. |
| Grade 3 | CT scan with lung windows pulmonary function testing includes: spirometry, DLCO, and room air O2 saturation at rest. Repeat at least every 6 weeks until return to within normal limits. Bronchoscopy with biopsy and/or BAL is recommended. | Consider corticosteroids if infective origin is ruled out. Taper as medically indicated. | Hold treatment with COMPOUND B/COMPOUND A until recovery to < Grade 1. May restart study treatment within 28 days at a reduced dose (by one level) if evidence of clinical benefit. |
| Grade 4 | CT scan with lung windows and required pulmonary function testing, if possible, includes: spirometry, DLCO, and room air O2 saturation at rest. Repeat at least every 6 weeks until return to within normal limits. Bronchoscopy with biopsy and/or BAL is recommended if possible. | Consider corticosteroids if infective origin is ruled out. Taper as medically indicated. | Discontinue treatment with COMPOUND B/COMPOUND A |

All dose modifications, interruptions or discontinuations are based on the worst preceding toxicity as graded by the NCI Clinical Toxicity Criteria for Adverse Events (NCI-CTCAE version 4.03). Once a dose is reduced during a treatment cycle, re-escalation is not permitted during any subsequent cycle. If administration of any drug is interrupted for reasons other than toxicity, treatment may be resumed at the same dose. If administration of any drug is interrupted due to unacceptable toxicity not described in table 1-1, treatment may be resumed at the same dose provided the toxicity resolved to ≤CTCAE grade 1 unless otherwise specified. After treatment is resumed at a lower dose (except for hyperglycemia), if the same toxicity recurs with the same severity, then the next treatment re-initiation must resume at a lower dose irrespective of duration.

To confirm the safety and tolerability of the drug doses, a strict monitoring for potential DLT and full PK analysis is performed on the first cohort of patients completing 2 cycles of treatment in ARM 1 and ARM 2. If 2 or more patients in the initial 6 patient cohort experience CLT, then the starting dose for subsequent patients will be 80 mg/day for COMPOUND A and 300 mg/day for COMPOUND B.

Patients continue on study treatment until disease progression, unacceptable toxicity or patient withdrawal. Comparative efficacy and safety evaluation is performed between ARM 1 and ARM 3 and between ARM 2 and ARM 3. No direct comparison is performed between ARM 1 and ARM 2.

To evaluate efficacy, tumor evaluation are determined locally according to the RECIST guidelines (RECIST Version 1.1) unless otherwise specified. The following radiologic and clinical assessments are performed:

Computed Tomography (CT) or Magnetic Resonance Imaging (MRI) of chest, abdomen and pelvis at screening and at each subsequent tumor evaluation.
The preferred radiologic technique is CT with intravenous (i.v.) contrast. If a patient is known to have a contraindication to CT contrast media or develops a contraindication during the trial, a non-contrast CT of the chest plus a contrast-enhanced MRI (if possible) of abdomen and pelvis should be performed.
A full body bone scan at screening for bone lesions according to institutional guidelines (e.g. Tc-99 bone scan, whole body bone MRI or sodium fluoride positron emission tomography (NaF PET).
If such a scan was already done during the regular work-up of the patient within 4 weeks prior to start of treatment, this scan can be considered as the screening scan for this study. After screening, scans need not be repeated, unless clinically indicated. If indicated, the same methodology as at screening should be used.
Localized CT, MRI or X-rays of all skeletal lesions identified on the screening bone scan, which are not visible on the chest, abdomen or pelvis CT (or MRI) must be taken at screening and at each subsequent tumor assessment.
Brain CT or MRI scan at screening if brain metastases are existing or suspected, brain CT or MRI will be continued at subsequent tumor evaluation if brain lesions are identified at screening.
Color photographs (with a ruler) if skin lesions are present at screening
Skin color photographs should be continued at subsequent tumor assessments for any lesions that were photographed at screening.
CT or MRI of any other site of disease not captured by any of the above listed images (e.g., neck) at screening and at each subsequent tumor evaluation. Ultrasound should not be used to measure tumor lesions.

Tumors are evaluated every 8 weeks from randomization until week 24 and then every 12 weeks until treatment end (±7 days).

Safety is monitored by assessing physical examination, vital signs, performance status evaluation, ECG, cardiac imaging, pulmonary function, laboratory evaluations for hematology and biochemistry (including glucose monitoring and assessment of patient's self-rated mood scales) and all serious and non-serious adverse events at every visit.

All patients who discontinue study treatment, including those who refuse to return for end of treatment visit, are contacted for safety evaualations (i.e, assessment of adverse events and/or serious adverse events, concomitant medications) for 28 days after the last dose of study treatment. Patients whose treatment is interrupted or permanently discontinued due to adverse event (including abnormal laboratory value) are followed until resolution or stabilization of the event, whichever comes first.

It is understood that the efficacy, safety and tolerability of the treatments may be assessed either at an interim timepoint (e.g, completion of the first 2 cycles of treatment by first 6 patients enrolled in ARM 1 and ARM 2) or upon completion of the study.

The invention claimed is:

1. A pharmaceutical combination comprising: (a) a phosphatidylinositol-3-kinase (PI3K) inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof, (b) a gonadorelin agonist goserelin or any pharmaceutically acceptable salt thereof, and (c) an antiestrogen agent tamoxifen or any pharmaceutically acceptable salt thereof.

2. A pharmaceutical combination according to claim 1, wherein the gonadorelin agonist is goserelin acetate.

3. A pharmaceutical combination according to claim 1, for simultaneous, separate or sequential use in the treatment of a cancer.

4. A method for treating a cancer in a subject in need thereof comprising administering to said subject a therapeutically effective amount of (a) a phosphatidylinositol-3-kinase (PI3K) inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof, (b) a gonadorelin agonist goserelin or any pharmaceutically acceptable salt thereof, and (c) an antiestrogen agent tamoxifen or any pharmaceutically acceptable salt thereof.

5. The method according to claim 4, wherein the cancer is a benign or malignant tumor of the breast.

6. A method according to claim 4, wherein the cancer is hormone-receptor positive breast cancer.

7. A combined preparation comprising: (a) one or more dosage units of a phosphatidylinositol-3-kinase inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or any pharmaceutically acceptable salt thereof, and (b) one or more dosage units of a gonadorelin agonist goserelin or any pharmaceutically acceptable salt thereof, and (c) one or more dosage units of an antiestrogen agent tamoxifen or any pharmaceutically acceptable salt thereof for use in the treatment of a cancer.

* * * * *